United States Patent
Guo et al.

(10) Patent No.: US 9,012,723 B2
(45) Date of Patent: Apr. 21, 2015

(54) ISOLATED NOVEL ACID AND PROTEIN MOLECULES FROM SOY AND METHODS OF USING THOSE MOLECULES TO GENERATE TRANSGENE PLANTS WITH ENHANCED AGRONOMIC TRAITS

(75) Inventors: Liang Guo, St. Louis, MO (US); David K. Kovalic, Clayton, MO (US); Bo-Xing Qiu, Chesterfield, MO (US); Jack E. Tabaska, O'Fallon, MO (US); Wei Wu, Chesterfield, MO (US)

(73) Assignee: Monsanto Technology LLC, St. Louis, MO (US)

( * ) Notice: Subject to any disclaimer, the term of this patent is extended or adjusted under 35 U.S.C. 154(b) by 729 days.

(21) Appl. No.: 13/138,181

(22) PCT Filed: Jan. 13, 2010

(86) PCT No.: PCT/US2010/020834
§ 371 (c)(1),
(2), (4) Date: Sep. 30, 2011

(87) PCT Pub. No.: WO2010/083179
PCT Pub. Date: Jul. 22, 2010

(65) Prior Publication Data
US 2012/0246748 A1    Sep. 27, 2012

Related U.S. Application Data

(60) Provisional application No. 61/205,230, filed on Jan. 16, 2009.

(51) Int. Cl.
*C12N 15/82* (2006.01)
*A01H 5/00* (2006.01)
*C12N 5/10* (2006.01)
*C12N 15/00* (2006.01)
*C07H 21/04* (2006.01)
*C07K 14/415* (2006.01)

(52) U.S. Cl.
CPC .......... *C07K 14/415* (2013.01); *C12N 15/8247* (2013.01); *C12N 15/8261* (2013.01)

(58) Field of Classification Search
None
See application file for complete search history.

(56) References Cited

U.S. PATENT DOCUMENTS

2007/0067865 A1*  3/2007  Kovalic et al. ................. 800/278

OTHER PUBLICATIONS

Guo Proc Natl Acad Sci 101 9205 2004.*
Whisstock_Q Rev Biophys_36_307_2003.*
International Search Report for PCT/US2010/020834 (forms 210 and 237); pp. 1-25.

* cited by examiner

*Primary Examiner* — Medina A Ibrahim
*Assistant Examiner* — Russell Boggs
(74) *Attorney, Agent, or Firm* — Lawrence M. Lavin, Jr.; David R. Marsh; Arnold & Porter LLP

(57) ABSTRACT

This disclosure provides purified nucleic acids and polypeptides. Also provided are transgenic plants, seeds, and plant cells containing DNA for expression of the proteins that are useful for imparting enhanced agronomic trait(s) to transgenic crop plants, methods of making such plants and methods of making agricultural commodity including seeds and hybrid seeds from such plants.

23 Claims, No Drawings

ISOLATED NOVEL ACID AND PROTEIN MOLECULES FROM SOY AND METHODS OF USING THOSE MOLECULES TO GENERATE TRANSGENE PLANTS WITH ENHANCED AGRONOMIC TRAITS

CROSS REFERENCE TO RELATED APPLICATIONS

This application is a national phase under 35 U.S.C. §371 of International Application No. PCT/US10/20834, filed on Jan. 13, 2010, which application claims benefit under 35 USC §119(e) of United States provisional application Ser. No. 61/205,230, filed on Jan. 16, 2009, which is incorporated herein by reference in its entirety.

INCORPORATION-BY-REFERENCE OF MATERIALS FILED ON COMPACT DISC

A sequence listing having the file name "38-21(56220)A-PCT_SeqListing.txt" was created on Jan. 7, 2010 and has 183,370 sequences and is herein incorporated by reference in its entirety. Per Box No. IX(g) of the PCT Request, form PCT/RO/101, the sequence listing will be filed separately on a physical data carrier, on the same day (Jan. 13, 2010), and in the form of an Annex C/ST.25 text file. The sequence listing will be sent to the Untied States Patent and Trademark Office by Express Mail No. EV736977070US.

TECHNICAL FIELD OF THE INVENTION

Disclosed herein are inventions in the field of plant genetics and developmental biology. More specifically, this invention provides novel compositions of corn DNA and peptide molecules. Also disclosed are plants comprising recombinant DNA providing one or more enhanced traits in a transgenic plant, including cells, seed, and pollen derived from such a plant, as well as methods of making and using such plant.

SUMMARY OF THE INVENTION

Certain embodiments of the disclosed invention provide recombinant DNA constructs having polynucleotides characterized by reference to SEQ ID NO: 1-91967 and the cognate proteins with amino acid sequences having reference to SEQ ID NO:91968-183370. The recombinant DNA constructs are used in aspects of the various embodiments of the invention to provide enhanced traits when stably integrated into the chromosomes and expressed in the nuclei of transgenic plants cells. In many aspects of these embodiments, the recombinant DNA constructs, when expressed in a plant cell, provide for expression of cognate proteins. In particular aspects of the invention the recombinant DNA constructs for expressing cognate proteins are characterized by cognate amino acid sequence that have at least 95% identity over at least 95% of the length of a reference sequence selected from the group consisting of SEQ ID NOs: 91968-183370 when the amino acid sequence is aligned to the reference sequence. In some aspects of the invention, the recombinant DNA constructs are characterized as being constructed with sense-oriented and/or anti-sense-oriented polynucleotides from the group consisting of SEQ ID NOs: 1-91967 which, when expressed in a plant cell, provide for the suppression of cognate proteins having amino acid sequences that have at least 95% identity over at least 95% of the length of a reference sequence selected from the group consisting of SEQ ID NOs: 91968-183370.

In certain aspects of this invention the recombinant DNA constructs of the invention are stably integrated into the chromosome of a plant cell nucleus.

Certain aspects of this embodiment of the invention provide transgenic plant cells having stably integrated recombinant DNA constructs, transgenic plants and seeds comprising a plurality of such transgenic plant cells and transgenic pollen of such plants. Such transgenic plants can be selected from a population of transgenic plants regenerated from plant cells transformed with recombinant DNA constructs by screening transgenic plants for an enhanced trait as compared to control plants. The enhanced trait provided may include, but is not limited to, enhanced water use efficiency, enhanced cold tolerance, increased yield, enhanced nitrogen use efficiency, altered seed protein composition, altered seed oil composition, or any combinations thereof.

Other embodiments of the invention provide for plant cells, plants, seeds, and pollen that can further comprise DNA expressing a protein that provides tolerance from exposure to an herbicide applied at levels that are lethal to a wild type plant cell.

Embodiments of the invention also provide methods for manufacturing non-natural, transgenic seed that can be used to produce a crop of transgenic plants with an enhanced trait resulting from expression of a stably-integrated recombinant DNA construct. The methods may comprise one or more of the following steps: (a) screening a population of plants for an enhanced trait and a recombinant DNA construct, where individual plants in the population can exhibit the trait at a level less than, essentially the same as or greater than the level that the trait is exhibited in control plants, (b) selecting from the population one or more plants that exhibit the trait at a level greater than the level that said trait is exhibited in control plants, (c) collecting seed from a selected plant, (d) verifying that the recombinant DNA is stably integrated in said selected plants, (e) analyzing tissue of a selected plant to determine the production or suppression of a protein having the function of a protein encoded by nucleotides in at least one sequence selected from SEQ ID NOs: 1-91967 or their complete complement thereof. In certain embodiments of the invention, the plants in the population further include DNA expressing a protein that provides tolerance to exposure to a herbicide applied at levels that are lethal to wild type plant cells and the selecting is affected by treating the population with the herbicide, e.g. a glyphosate, dicamba, or glufosinate compound. In another embodiment of the invention, the plants are selected by identifying plants with the enhanced trait. The methods can be used for the manufacturing corn, soybean, cotton, canola, alfalfa, wheat, rice, sugarcane or sugar beet seed. In other embodiments of the present invention, the methods can also be used for manufacture transgenic plants including, but are not limited to, millet, barley, peanut, pigeon pea, sorghum, vegetables (including but not limited to Broccoli, Cauliflower, Cabbage, Radish, Chinese cabbage, Melons, Watermelons, Cucumber, Gourds, Pumpkin, Squash, Pepper, Tomato, Eggplant, Onion, Carrot, Garden Bean, Sweet Corn, Pea, Dry Bean, Okra, Spinach, Leek, Lettuce, and Fennel), grape, berries (including blue, black, raspberry, mullberry, boisenberry, etc), cherry and related fruit trees (including but not limited to plum, peach, apricot, kiwi, pomegranate, mango, fig), fruit trees (including but not limited to orange, lemon, lime, blood orange, grapefruit, and the like), and nut trees (including but not limited to coconut, walnut (English and black), pecan, almond, hazelnut, brazil nut, hickory nut, acorn, and the like) and sunflower, other oilseed producing plants or any combinations thereof.

Other embodiments of the invention provide a methods for producing hybrid corn seed by acquiring hybrid corn seed from a herbicide tolerant corn plant which also has stably-integrated, recombinant DNA construct having a promoter that is (a) functional in plant cells and (b) is operably linked to DNA that encodes or suppresses a protein having the function of a protein encoded by nucleotides in at least one sequence selected from the group consisting of SEQ ID NOs: 1-91967. The methods of these embodiments may further include producing corn plants from said hybrid corn seed, wherein a fraction of the plants produced from said hybrid corn seed is homozygous for said recombinant DNA, a fraction of the plants produced from said hybrid corn seed is hemizygous for said recombinant DNA, and a fraction of the plants produced from said hybrid corn seed has none of said recombinant DNA; selecting corn plants which are homozygous and hemizygous for said recombinant DNA by treating with an herbicide; collecting seed from herbicide-treated-surviving corn plants and planting said seed to produce further progeny corn plants; repeating the selecting and collecting steps at least once to produce an inbred corn line; and crossing the inbred corn line with a second corn line to produce hybrid seed.

Other embodiments of the invention provide methods for selecting a plant comprising plant cells of the invention by using an immunoreactive antibody to detect the presence or absence of protein expressed or suppressed by recombinant DNA in seed or plant tissue. Another embodiment of the invention provides anti-counterfeit milled seed having, as an indication of origin, plant cells of this invention.

Still other embodiments of this invention provide for transgenic plants with enhanced water use efficiency or enhanced nitrogen use efficiency. For example, this invention provides methods of growing a corn, cotton, soybean, or canola crop without irrigation water by planting seed having plant cells of the invention which are selected for enhanced water use efficiency. Alternatively embodiments of these methods include applying reduced irrigation water, e.g. providing up to 300 millimeters of ground water during the production of a corn crop. This invention also provides methods of growing a corn, cotton, soybean or canola crop without added nitrogen fertilizer by planting seed having plant cells of the invention which are selected for enhanced nitrogen use efficiency.

Other embodiments of the invention provide mixtures comprising plants cells and an antibody to a protein produced in the cells where the protein has an amino acid sequence that has at least 90% identity over at least 90% of the length of a reference sequence selected from the group consisting of SEQ ID NO: 91968-183370 when the sequence is aligned to the reference sequence.

In another aspect, the present invention includes a mixture having plant cells, and an antibody to a protein produced in said cells wherein said protein has an amino acid sequence that has at least 95% identity over at least 95% of the length of a reference sequence selected from the group consisting of SEQ ID NO: 91968-183370 when said amino acid sequence is aligned to said reference sequence.

In another aspect, the present invention includes a mixture having plant cells, and an antibody to a protein produced in said cells wherein said protein has an amino acid sequence that has at least 98% identity over at least 98% of the length of a reference sequence selected from the group consisting of SEQ ID NO: 91968-183370 when said amino acid sequence is aligned to said reference sequence.

In another aspect, the present invention includes a mixture having plant cells, and an antibody to a protein produced in said cells wherein said protein has an amino acid sequence that has at least 99% identity over at least 99% of the length of a reference sequence selected from the group consisting of SEQ ID NO: 91968-183370 when said amino acid sequence is aligned to said reference sequence.

In another aspect, the present invention includes a mixture having plant cells, and an antibody to a protein produced in said cells wherein said protein has an amino acid sequence that has at least 99.5% identity over at least 99.5% of the length of a reference sequence selected from the group consisting of SEQ ID NO: 91968-183370 when said amino acid sequence is aligned to said reference sequence.

Yet another aspect of the present invention includes a transgenic plant cell with stably integrated, recombinant DNA comprising a promoter that is functional in plant cells and that is operably linked to DNA from a plant, bacteria or yeast that encodes a protein having at least 90% sequence identity selected from the group consisting of SEQ ID NO: 91968-183370; wherein said plant cell is selected from a population of plant with said recombinant DNA by screening plants that are regenerated from plant cells in said population and that express said protein for an enhanced trait as compared to control plants that do not have said recombinant DNA; and wherein said enhanced trait includes, but are not limited to, enhanced water use efficiency, enhanced cold tolerance, increased yield, enhanced nitrogen use efficiency, enhanced seed protein or enhanced seed oil.

ILLUSTRATIVE EMBODIMENTS OF THE INVENTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

In the Attached Sequence Listing:

SEQ ID NO:1-91967 are nucleotide sequences of the coding strand of DNA for "genes" used in the recombinant DNA imparting an enhanced trait in plant cells, e.g. each comprises a coding sequence for a protein;

SEQ ID NO: 91968-183370 are amino acid sequences of the cognate protein of the "genes" with nucleotide coding sequences provided by SEQ ID NO: 1-91967;

As used herein, a "plant cell" means a plant cell that is transformed with stably-integrated, non-natural, recombinant DNA, e.g. by *Agrobacterium*-mediated transformation or by bombardment using microparticles coated with recombinant DNA or other means. A plant cell of this invention can be an originally-transformed plant cell that exists as a microorganism or as a progeny plant cell that is duplicated by regeneration into differentiated tissue, e.g. into a transgenic plant with stably-integrated, non-natural recombinant DNA, or seed or pollen derived from a progeny transgenic plant.

As used herein, a "transgenic plant" means a plant whose genome has been altered by the stable integration of recombinant DNA. A transgenic plant includes a plant regenerated from an originally-transformed plant cell and progeny transgenic plants from later generations or crosses of a transformed plant.

A "consensus amino acid sequence" means an artificial, amino acid sequence indicating conserved amino acids in the sequence of homologous proteins as determined by statistical analysis of an optimal alignment, e.g. CLUSTALW, of amino acid sequence of homolog proteins. The consensus sequences listed in the sequence listing were created by identifying the most frequent amino acid at each position in a set of aligned protein sequences. When there was 100% identity in an alignment the amino acid is indicated by a capital letter. When the occurrence of an amino acid is at least about 70% in an alignment, the amino acid is indicated by a lower case letter. When there is no amino acid occurrence of at least about 70%, e.g. due to diversity or gaps, the amino acid is indicated by an "x". When used to defined embodiments of the invention, a consensus amino acid sequence will be aligned with a query protein amino acid sequence in an optimal alignment, e.g. CLUSTALW. An embodiment of the invention will have identity to the conserved amino acids indicated in the consensus amino acid sequence.

As used herein, "control plant" means a plant that does not contain the recombinant DNA that expressed a protein which imparts an enhanced trait. A control plant is to identify and select a transgenic plant that has an enhance trait. A suitable control plant can be a non-transgenic plant of the parental line used to generate a transgenic plant, e.g., devoid of recombinant DNA. A suitable control plant can in some cases be a progeny of a hemizygous transgenic plant line that is does not contain the recombinant DNA, known as a negative segregant.

As used herein, an "enhanced trait" means a characteristic of a transgenic plant that includes, but is not limited to, an enhance agronomic trait characterized by enhanced plant morphology, physiology, growth and development, yield, nutritional enhancement, disease or pest resistance, or environmental or chemical tolerance. In more specific aspects of this invention enhanced trait is selected from group of enhanced traits consisting of enhanced water use efficiency, enhanced cold tolerance, increased yield, enhanced nitrogen use efficiency, enhanced seed protein and enhanced seed oil. In an important aspect of the invention the enhanced trait is enhanced yield including increased yield under non-stress conditions and increased yield under environmental stress conditions. Stress conditions can include, for example, drought, shade, fungal disease, viral disease, bacterial disease, insect infestation, nematode infestation, cold temperature exposure, heat exposure, osmotic stress, reduced nitrogen nutrient availability, reduced phosphorus nutrient availability and high plant density. "Yield" can be affected by many properties including without limitation, plant height, pod number, pod position on the plant, number of internodes, incidence of pod shatter, grain size, efficiency of nodulation and nitrogen fixation, efficiency of nutrient assimilation, resistance to biotic and abiotic stress, carbon assimilation, plant architecture, resistance to lodging, percent seed germination, seedling vigor, and juvenile traits. Yield can also be affected by efficiency of germination (including germination in stressed conditions), growth rate (including growth rate in stressed conditions), ear number, seed number per ear, seed size, composition of seed (starch, oil, protein) and characteristics of seed fill.

Increased yield of a transgenic plant of the present invention can be measured in a number of ways, including test weight, seed number per plant, seed weight, seed number per unit area (e.g., seeds, or weight of seeds, per acre), bushels per acre, tonnes per acre, tons per acre, kilo per hectare. For example, maize yield can be measured as production of shelled corn kernels per unit of production area in bushels per acre or metric tons per hectare, often reported on a moisture adjusted basis at about 15.5 percent moisture. Increased yield can result from improved utilization of key biochemical compounds such as nitrogen, phosphorous and carbohydrate, or from improved responses to environmental stresses, such as cold, heat, drought, salt, and attack by pests or pathogens. Recombinant DNA used in this invention can also be used to provide plants having improved growth and development, and ultimately increased yield, as the result of modified expression of plant growth regulators or modification of cell cycle or photosynthesis pathways. Also of interest is the generation of transgenic plants that demonstrate enhanced yield with respect to a seed component that can correspond to an increase in overall plant yield. Such properties include enhancements in seed oil, seed molecules such as tocopherol, protein and starch, or oil, particular oil components as can be manifest by alterations in the ratios of seed components.

Seed according to the present invention may be planted, grown and harvested to produce a crop or terminal crop. As used herein, a "crop" is a plant or plant product that is grown and harvested, such plant or plant product including but not limited to plants or plant parts such as leaf, root, shoot, fruit, seed, grain, or the like. A "terminal crop" is a crop grown for uses other than for use as planting seed to produce subsequent generations of plants. In some crop plants, such as grain produced from hybrid corn, the crop is not very suitable for planting because it does not breed true and the crop can then be conveniently referred to as "hybrid grain." In other crop plants, where the crop does breed true, such as soybean, whether a crop is planting seed or a terminal crop will depend on the uses and marketing channels of the crop. If used or marketed for planting, it will be a crop of planting seed; if used or marketed for other purposes it will be a terminal crop.

As used herein, "exogenous promoter region" refers to a sequence, capable of promoting mRNA transcription, that does not naturally occur in the plant at the same site and/or linked to the nucleic acids. The promoter can be from a different plant species or it can be from the same plant species, but naturally found in a different location in a non-genetically modified plant. Moreover, the promoter region can be found in the same genetic locus as is present a native plant, but linked to different sequence(s), than are native.

As used herein, "promoter" means regulatory DNA for initializing transcription. A "plant promoter" is a promoter capable of initiating transcription in plant cells whether or not its origin is a plant cell, e.g. is it well known that *Agrobacterium* promoters are functional in plant cells. Thus, plant promoters include promoter DNA obtained from plants, plant viruses and bacteria such as *Agrobacterium* and *Bradyrhizobium* bacteria. Examples of promoters under developmental control include promoters that preferentially initiate transcription in certain tissues, such as leaves, roots, or seeds. Such promoters are referred to as "tissue preferred". Promoters that initiate transcription only in certain tissues are referred to as "tissue specific". A "cell type" specific promoter primarily drives expression in certain cell types in one or more organs, for example, vascular cells in roots or leaves. An "inducible" or "repressible" promoter is a promoter which is under environmental control. Examples of environmental conditions that can effect transcription by inducible promoters include anaerobic conditions, or certain chemicals, or the presence of light. Tissue specific, tissue preferred, cell-type specific, and inducible promoters constitute the class of "nonconstitutive" promoters. A "constitutive" promoter is a promoter which is active under most conditions.

As used herein, a "functional fragment" refers to a portion of a polypeptide provided herein which retains full or partial molecular, physiological or biochemical function of the full length polypeptide. A functional fragment often contains the domain(s), such as Pfam domain, identified in the polypeptide provided in the sequence listing. In some embodiment, a function fragment includes at least 1, 2, 3, 4, 5 or more starting coding codons and at least 1, 2, 3, 4, 5 or more stop codons.

Embodiments of the invention provide molecules of that include "fragments" of the disclosed recombinant DNA molecules; including oligonucleotides of at least 15, at least 16 or 17, at least 18 or 19, and at least 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more, consecutive nucleotides of any of the sequences provided. Such oligonucleotides are fragments of the larger molecules having a sequence selected from the group consisting of SEQ ID NO: 1 through SEQ ID NO: 91967, and find use, for example as probes and primers for detection of the polynucleotides of the present invention. Alternatively, these fragments can be used as RNAi for gene suppression purposes. In some embodiments, a fragment can contain one or more coding region. In another embodiment, a fragment can include non-coding regions only.

Aspects of the various embodiments of the invention also provide for nucleic acid fragments of SEQ ID NO: 1 through SEQ ID NO: 91967 that are at least about 125, 150, 175, 200, 225, 250, 300, 325, 350, 375, 400, 425, 450, 475, 500, 525, 550, 575, 600, 625, 650, 675, 700, 725, 750, 775, 800, 825, 850, 875, 900, 925, 950, 975, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2150, 2200, 2250, 2300, 2350, 2400, 2450, 2500, 2550, 2600, 2650, 2700, 2750, 2800, 2850, 2900, 2950, 3000 or more nucleotides in length. Some aspects of these embodiments provide for nucleic acid fragment molecules that encode functional fragment of any of the polypeptide sequences provided in SEQ ID NO: 91968 to SEQ ID NO: 183370.

Other embodiments of the present invention provide for one or more polypeptides having at least about 10 contiguous peptide residues of one or more of the peptide sequences provided in SEQ ID NO: 91968 to SEQ ID NO: 183370. In other aspects of these embodiment, the polypeptide(s) comprises at least 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 525, 550, 575, 600, 625, 650, 675, 700, 750, 800, 850, 900, 950, 1000 or more contiguous peptide residues from one or more of the sequences provided in SEQ ID NO: 91968 to SEQ ID NO: 183370. In particularly aspects, these embodiments the poly peptide includes a functional fragment of one or more of the polypeptides provided in the Sequence Listing.

The present invention also provides substantial, credible, and specific utility of each nucleic acid and amino acid molecules disclosed in the sequence listing. For example, SEQ ID No. 163320 is annotated as nitric-oxide synthase in the sequence listing. This correlation indicates SEQ ID No. 163320 has substantial, credible, and specific utility.

As used herein, "expressed" means produced, e.g. a protein is expressed in a plant cell when its cognate DNA is transcribed to mRNA that is translated to the protein.

As used herein, an "expression cassette of a DNA construct" is capable of integrating in a plant genome, expressing a functional polypeptide and providing a transgenic plant expressing polypeptides of the invention.

As used herein, "suppressed" means decreased, e.g. a protein is suppressed in a plant cell when there is a decrease in the amount and/or activity of the protein in the plant cell. The presence or activity of the protein can be decreased by any amount up to and including a total loss of protein expression and/or activity.

As used herein, a "functional fragment" refers to a portion of a polypeptide provided herein which retains full or partial molecular, physiological or biochemical function of the full length polypeptide. A functional fragment often contains the domain(s), such as Pfam domain, identified in the polypeptide provided in the sequence listing.

As used herein, a "homolog" means a protein in a group of proteins that perform the same biological function, e.g. proteins that belong to the same Pfam protein family and that provide a common enhanced trait in transgenic plants of this invention. Homologs are expressed by homologous genes. With reference to homologous genes, homologs include orthologs, e.g., genes expressed in different species that evolved from a common ancestral genes by speciation and encode proteins retain the same function, but do not include paralogs, e.g., genes that are related by duplication but have evolved to encode proteins with different functions. Homologous genes include naturally occurring alleles and artificially-created variants. Degeneracy of the genetic code provides the possibility to substitute at least one base of the protein encoding sequence of a gene with a different base without causing the amino acid sequence of the polypeptide produced from the gene to be changed. When optimally aligned, homolog proteins have typically at least about 60% identity, in some instances at least about 70%, at least about 75%, at least about bout 80%, about 85%, at least about 90%, at least about bout 92%, at least about bout 94%, at least about bout 95%, at least about 96%, at least about 97%, at least about 98%, at least about 99%, and even at least about 99.5% identity over the full length of a protein identified as being associated with imparting an enhanced trait when expressed in plant cells. In one aspect of the invention homolog proteins have an amino acid sequence that has at least about 80%, at least about 85%, at least about 90%, at least about 92.5%, at least about 95%, at least about 96%, at least about 97%, at least about 98%, at least about 99%, and at least about 99.5% identity to a consensus amino acid sequence of proteins and homologs that can be build from sequences disclosed herein.

Homologs can be identified by comparison of amino acid sequence, e.g. manually or by use of a computer-based tool using known homology-based search algorithms such as those commonly known and referred to as BLAST, FASTA, and Smith-Waterman. A local sequence alignment program, e.g. BLAST, can be used to search a database of sequences to find similar sequences, and the summary Expectation value (E-value) used to measure the sequence base similarity. Because a protein hit with the best E-value for a particular organism may not necessarily be an ortholog, e.g., have the same function, or be the only ortholog, a reciprocal query is used to filter hit sequences with significant E-values for ortholog identification. The reciprocal query entails search of the significant hits against a database of amino acid sequences from the base organism that are similar to the sequence of the query protein. A hit can be identified as an ortholog, when the reciprocal query's best hit is the query protein itself or a protein encoded by a duplicated gene after speciation. A further aspect of the homologs encoded by DNA useful in the transgenic plants of the invention are those proteins that differ from a disclosed protein as the result of deletion or insertion of one or more amino acids in a native sequence.

Other functional homolog proteins differ in one or more amino acids from those of a trait-improving protein disclosed herein as the result of one or more of the well-known conservative amino acid substitutions, e.g., valine is a conservative substitute for alanine and threonine is a conservative substitute for serine. Conservative substitutions for an amino acid within the native sequence can be selected from other members of a class to which the naturally occurring amino acid belongs. Representative amino acids within these various classes include, but are not limited to: (1) acidic (negatively charged) amino acids such as aspartic acid and glutamic acid; (2) basic (positively charged) amino acids such as arginine, histidine, and lysine; (3) neutral polar amino acids such as glycine, serine, threonine, cysteine, tyrosine, asparagine, and glutamine; and (4) neutral nonpolar (hydrophobic) amino acids such as alanine, leucine, isoleucine, valine, proline, phenylalanine, tryptophan, and methionine. Conserved substitutes for an amino acid within a native amino acid sequence can be selected from other members of the group to which the naturally occurring amino acid belongs. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Naturally conservative amino acids substitution groups are: valine-leucine, valine-isoleucine, phenylalanine-tyrosine, lysine-arginine, alanine-valine, aspartic acid-glutamic acid, and asparagine-glutamine. A further aspect of the invention includes proteins that differ in one or more amino acids from those of a described protein sequence as the result of deletion or insertion of one or more amino acids in a native sequence.

Genes that are homologous to each other can be grouped into families and included in multiple sequence alignments. Then a consensus sequence for each group can be derived. This analysis enables the derivation of conserved and class—(family) specific residues or motifs that are functionally important. These conserved residues and motifs can be further validated with 3D protein structure if available. The consensus sequence can be used to define the full scope of the invention, e.g., to identify proteins with a homolog relationship. Thus, the present invention contemplates that protein homologs include proteins with an amino acid sequence that has at least 90% identity to such a consensus amino acid sequence sequences.

As used herein, "operably linked" refers to the association of two or more nucleic acid elements in a recombinant DNA construct, e.g. as when a promoter is operably linked with DNA that is transcribed to RNA whether for expressing or suppressing a protein. Recombinant DNA constructs can be designed to express a protein which can be an endogenous protein, an exogenous homologue of an endogenous protein or an exogenous protein with no native homologue. Alternatively, recombinant DNA constructs can be designed to suppress the level of an endogenous protein, e.g. by suppression of the native gene. Such gene suppression can be effectively employed through a native RNA interference (RNAi) mechanism in which recombinant DNA comprises both sense and anti-sense oriented DNA matched to the gene targeted for suppression where the recombinant DNA is transcribed into RNA that can form a double-strand to initiate an RNAi mechanism. Gene suppression can also be effected by recombinant DNA that comprises anti-sense oriented DNA matched to the gene targeted for suppression. Gene suppression can also be effected by recombinant DNA that comprises DNA that is transcribed to a microRNA matched to the gene targeted for suppression. In the examples illustrating the invention recombinant DNA for effecting gene suppression that imparts is identified by the term "antisense". It will be understood by a person of ordinary skill in the art that any of the ways of effecting gene suppression are contemplated and enabled by a showing of one approach to gene suppression.

As used herein, "percent identity" means the extent to which two optimally aligned DNA or protein segments are invariant throughout a window of alignment of components, for example nucleotide sequence or amino acid sequence. An "identity fraction" for aligned segments of a test sequence and a reference sequence is the number of identical components that are shared by sequences of the two aligned segments divided by the total number of sequence components in the reference segment over a window of alignment which is the smaller of the full test sequence or the full reference sequence. "Percent identity" ("% identity") is the identity fraction times 100. Such optimal alignment is understood to be deemed as local alignment of DNA sequences. For protein alignment, a local alignment of protein sequences should allow introduction of gaps to achieve optimal alignment. Percent identity is calculated over the aligned length not including the gaps introduced by the alignment per se.

As used herein, a "plant by-product" includes any product that is made from a plant or plant product, for example, by dehulling, crushing, milling, extraction, hydrogenation, and other processes. A plant by-products in accordance with the invention, therefore, will include such as, for example, dehulled soybeans, crushed corn, soybean meal, soy milk, paper made from corn stalks, and a wide range of other useful products of processing based on plant vitamins, minerals, lipids, proteins and carbohydrates and their constituents that can be characterized as being produced from crops or terminal crops in accordance with the invention.

As used herein, a "plant cell" means a plant cell that is transformed with stably-integrated, recombinant DNA, e.g. by *Agrobacterium*-mediated transformation or by bombardment using microparticles coated with recombinant DNA or other means. A plant cell of this invention can be an originally-transformed plant cell that exists as a microorganism or as a progeny plant cell that is regenerated into differentiated tissue, e.g.

into a transgenic plant with stably-integrated, non-natural recombinant DNA, or seed or pollen derived from a progeny transgenic plant.

As used herein, the term "polypeptide" or "polypeptide molecule" means a chain of amino acids. Polypeptide is also commonly referred as "protein".

As used herein, "polyadenylated ribonucleotides" refers to the series of adenosines at the 3' end of a polyribonucleotide commonly referred to as a "poly-A tail".

As used herein, "recombinant DNA" means DNA which has been genetically engineered and constructed outside of a cell including DNA containing naturally occurring DNA or cDNA or synthetic DNA.

As used herein, the term "structural nucleic acid molecule" refers to a molecule having sequence that encodes a protein, functional peptide fragment, or any other molecule that has biological activity (including, but not limited to, mRNA and bioactive RNA molecules, including antisense RNA).

As used herein, the term "substantially purified nucleic acid" or polypeptide means nucleic acid or protein separated from substantially all other molecules normally associated with it in its native state. A substantially purified nucleic acid can be greater than about 60% free from the other molecules (exclusive of solvent) present in the natural mixture. The term "substantially purified" is not intended to encompass molecules present in their native state.

"Pfam" database is a large collection of multiple sequence alignments and hidden Markov models covering many common protein families, e.g. Pfam version 19.0 (December 2005) contains alignments and models for 8183 protein families and is based on the Swissprot 47.0 and SP-TrEMBL 30.0 protein sequence databases. See S. R. Eddy, "Profile Hidden Markov Models", *Bioinformatics* 14:755-763, 1998. The Pfam database is currently maintained and updated by the Pfam Consortium. The alignments represent some evolutionary conserved structure that has implications for the protein's function. Profile hidden Markov models (profile HMMs) built from the protein family alignments are useful for automatically recognizing that a new protein belongs to an existing protein family even if the homology by alignment appears to be low.

The modulation of protein in transgenic plant cells (hereafter generally referred to as the "target protein") can be achieved by a variety of approaches involving the use of recombinant DNA constructs. Examples of such recombinant DNA constructs include recombinant DNA constructs that produce messenger RNA for the target protein where native miRNA recognition sites in the mRNA for the target protein are modified or deleted, recombinant DNA constructs that produce an RNA gene suppression element such as a miRNA or a dsRNA comprising sense and anti-sense sequences from the gene encoding the target protein, recombinant DNA constructs that produce a transacting short interfering RNA (ta-siRNA) and recombinant DNA constructs that produce a miRNA element such as a decoy miRNA that is a target for native miRNA or RNA that sequesters target messenger RNA away from native miRNA.

Small RNAs that regulate protein expression include miRNAs and ta-siRNAs. A miRNA is a small (typically about 21 nucleotide) RNA that has the ability to modulate the expression of a target gene by binding to messenger RNA for the target protein leading to destabilization of the target protein messenger RNA or translational inhibition of the target protein messenger RNA, ultimately resulting in reduction of the target protein. The design and construction of ta-siRNA constructs and their use in the modulation of protein in transgenic plant cells is disclosed by Allen and Carrington in US Patent Application Publication US 2006/0174380 A1 which is incorporated herein by reference. The expression or suppression of such small RNAs are aspects of the invention that are conveniently illustrated by reference to use of miRNAs.

Recombinant DNA constructs can be used to modify the activity of native miRNAs by a variety of means. By increasing the expression of a miRNA, e.g. temporally or spatially, the modulation of expression of a native target gene can be enhanced. An alternative gene suppression approach for suppressing the expression of a target protein can include the use of a recombinant DNA construct that produces a synthetic miRNA that is designed to bind to a native or synthetic miRNA recognition site on messenger RNA for the target protein.

By reducing the expression of a miRNA, the modulation of a native target gene can be diminished resulting in enhanced expression of the target protein. More specifically, the expression of a target protein can be enhanced by suppression of the activity of the miRNA that binds to a recognition site in the messenger RNA that is transcribed from the native gene for the target protein. Several types of recombinant DNA constructs can be designed to suppress the activity of a miRNA.

For example, a recombinant DNA construct that produces an abundance of RNA with the miRNA recognition site can be used as a decoy for the native miRNA allowing endogenous messenger RNA with the miRNA recognition site to be translated to the target protein without interference from native miRNA. A recombinant DNA construct that produces RNA with a modified miRNA recognition site, e.g. with nucleotides at positions 10 and/or 11 in a 21mer miRNA recognition site which are unpaired with respect to the native miRNA, can be used to sequester natively expressed miRNA thereby reducing the cleavage that normally occurs when miRNA binds to a recognition site. The unpaired nucleotides can be produced e.g. through additional nucleotides between positions 10 and 11 or through substitutions of the nucleotides at positions 10 and 11.

Additionally, a recombinant DNA construct can be created that produces RNA that can be processed in plants into synthetic small RNA (miRNA-like) that can bind endogenous miRNA recognition sites but is unable to induce cleavage of mRNA because the small RNA is modified, for instance by having a modified nucleotide at positions 10 and/or 11 or a deletion that produces a bulge between positions 10 and 11 when the small RNA is paired with the miRNA recognition site. The resulting synthetic small RNA, a cleavage blocker, can reduce endogenous miRNA binding and thus block cleavage of a protected miRNA target site enhancing the expression of a target protein.

A recombinant DNA construct designed for producing a modified messenger RNA for the protein where the native miRNA recognition site is modified to be resistant to the binding of cognate miRNA which regulates the native gene can also be used to express protein from heterologous messenger RNA that is no longer modulated by the native miRNA.

The activity of a miRNA which down-regulates an endogenous protein is enhanced by enhancing the expression of the miRNA or by enhancing the ability of the miRNA to bind an RNA encoding the target protein. A recombinant DNA encoding an RNA encoding the miRNA or a miRNA-sensitive messenger RNA encoding the protein in which a miRNA binding site is added are designed to enhance miRNA activity resulting in enhanced suppression of the target mRNA and cognate protein. Recombinant DNA encoding an RNA encoding a miRNA, or a miRNA-sensitive RNA are designed using methods disclosed in U.S. Patent Application Publication U.S. 2009/0070898 A1.

Some, if not many, miRNAs modulate the expression of multiple proteins or biochemical pathways. Transgenic plants can be provided with enhanced traits not so much from the suppression or enhancement of the expression of a particular protein, as from change of enzyme activity in a pathway by modulating the level of a miRNA. Thus, aspects of this invention are achieved by enhanced miRNA activity resulting from use in transgenic plant cells of recombinant DNA constructs that produce an enhanced level of a miRNA. Other aspects of this invention are achieved by reduced miRNA activity resulting from use in transgenic plant cells of recombinant DNA constructs that produce a reduced level or activity of a miRNA.

Recombinant DNA Constructs

Recombinant DNA constructs are assembled using methods well known to persons of ordinary skill in the art and typically comprise a promoter operably linked to DNA, the expression of which provides the enhanced agronomic trait. Other construct components can include additional regulatory elements, such as 5' leaders and introns for enhancing transcription, 3' untranslated regions (such as polyadenylation signals and sites), DNA for transit or signal peptides.

Numerous promoters that are active in plant cells have been described in the literature. These include promoters present in plant genomes as well as promoters from other sources, including nopaline synthase (NOS) promoter and octopine synthase (OCS) promoters carried on tumor-inducing plasmids of *Agrobacterium tumefaciens* and the CaMV35S promoters from the cauliflower mosaic virus as disclosed in U.S. Pat. Nos. 5,164, 316 and 5,322,938. Useful promoters derived from plant genes are found in U.S. Pat. No. 5,641,876 which discloses a rice actin promoter, U.S. Pat. No. 7,151,204 which discloses a maize chloroplast aldolase promoter and a maize aldolase (FDA) promoter, and U.S. Patent Application Publication 2003/0131377 A1 which discloses a maize nicotianamine synthase promoter. These and numerous other promoters that function in plant cells are known to those skilled in the art and available for use in recombinant polynucleotides of the present invention to provide for expression of desired genes in transgenic plant cells.

Furthermore, the promoters can be altered to contain multiple "enhancer sequences" to assist in elevating gene expression. Such enhancers are known in the art. By including an enhancer sequence with such constructs, the expression of the selected protein can be enhanced. These enhancers often are found 5' to the start of transcription in a promoter that functions in eukaryotic cells, but can often be inserted upstream (5') or downstream (3') to the coding sequence. In some instances, these 5' enhancing elements are introns. Particularly useful as enhancers are the 5' introns of the rice actin 1 (see U.S. Pat. No. 5,641,876) and rice actin 2 genes, the maize alcohol dehydrogenase gene intron, the maize heat shock protein 70 gene intron (U.S. Pat. No. 5,593,874) and the maize shrunken 1 gene. See also U.S. Patent Application Publication 2002/0192813A1 which discloses 5', 3' and intron elements useful in the design of effective plant expression vectors.

In other aspects of the invention, sufficient expression in plant seed tissues is desired to affect improvements in seed composition. Exemplary promoters for use for seed composition modification include promoters from seed genes such as napin as disclosed in U.S. Pat. No. 5,420,034, maize L3 oleosin as disclosed in U.S. Pat. No. 6,433,252), zein Z27 as disclosed by Russell et al. (1997) *Transgenic Res.* 6(2):157-166), globulin 1 as disclosed by Belanger et al (1991) *Genetics* 129:863-872), glutelin 1 as disclosed by Russell (1997) supra), and peroxiredoxin antioxidant (Per1) as disclosed by Stacy et al. (1996) *Plant Mol Biol.* 31(6):1205-1216.

Recombinant DNA constructs in this invention will generally include a 3' element that typically contains a polyadenylation signal and site. Well-known 3' elements include those from *Agrobacterium tumefaciens* genes such as nos 3', tml 3', tmr 3', tms 3', ocs 3', tr7 3', for example disclosed in U.S. Pat. No. 6,090,627; 3' elements from plant genes such as wheat (*Triticum aesevitum*) heat shock protein 17 (Hsp17 3'), a wheat ubiquitin gene, a wheat fructose-1,6-biphosphatase gene, a rice glutelin gene, a rice lactate dehydrogenase gene and a rice beta-tubulin gene, all of which are disclosed in U.S. Patent Application Publication No. 2002/0192813 A1; and the pea (*Pisum sativum*) ribulose biphosphate carboxylase gene (rbs 3'), and 3' elements from the genes within the host plant.

Constructs and vectors can also include a transit peptide for targeting of a gene to a plant organelle, particularly to a chloroplast, leucoplast or other plastid organelle. For descriptions of the use of chloroplast transit peptides see U.S. Pat. No. 5, 188,642 and U.S. Pat. No. 5,728,925. For description of the transit peptide region of an Arabidopsis EPSPS gene useful in the present invention, see Klee, H. J. et al (MGG (1987) 210:437-442).

Recombinant DNA constructs for gene suppression can be designed for any of a number the well-known methods for suppressing transcription of a gene, the accumulation of the mRNA corresponding to that gene or preventing translation of the transcript into protein. Posttranscriptional gene suppression can be practically effected by transcription of RNA that forms double-stranded RNA (dsRNA) having homology to mRNA produced from a gene targeted for suppression.

Gene suppression can also be achieved by insertion mutations created by transposable elements can also prevent gene function. For example, in many dicot plants, transformation with the T-DNA of *Agrobacterium* can be readily achieved and large numbers of transformants can be rapidly obtained. Also, some species have lines with active transposable elements that can efficiently be used for the generation of large numbers of insertion mutations, while some other species lack such options. Mutant plants produced by *Agrobacterium* or transposon mutagenesis and having altered expression of a polypeptide of interest can be identified using the polynucleotides of the present invention. For example, a large population of mutated plants can be screened with polynucleotides encoding the polypeptide of interest to detect mutated plants having an insertion in the gene encoding the polypeptide of interest.

Transgenic plants comprising or derived from plant cells of this invention transformed with recombinant DNA can be further enhanced with stacked traits, e.g. a crop plant having an enhanced trait resulting from expression of DNA disclosed herein in combination with other enhanced traits with various degree or amount of enhancement including, but not limited to enhanced water use efficiency, enhanced cold tolerance, increased yield, enhanced nitrogen use efficiency, enhanced seed protein and enhanced seed oil herbicide pest resistance traits, or any combinations thereof. For example, genes of the current invention can be stacked with other traits of agronomic interest, such as a trait providing herbicide resistance, or insect resistance, such as using a gene from *Bacillus thuringensis* to provide resistance against lepidopteran, coliopteran, homopteran, hemiopteran, and other insects. Herbicides for which transgenic plant tolerance has been demonstrated and the method of the present invention can be applied include, but are not limited to, glyphosate, dicamba, glufosinate, sulfonylurea, bromoxynil and norflurazon herbicides. Polynucleotide molecules encoding proteins involved in herbicide tolerance are well-known in the art and include, but are not limited to, a polynucleotide molecule encoding 5-enolpyruvylshikimate-3-phosphate synthase (EPSPS) disclosed in U.S. Pat. Nos. 5,094,945; 5,627,061; 5,633,435 and 6,040,497 for imparting glyphosate tolerance; polynucleotide molecules encoding a glyphosate oxidoreductase (GOX) disclosed in U.S. Pat. No. 5,463,175 and a glyphosate-N-acetyl transferase (GAT) disclosed in U.S. Patent Application Publication No. 2003/0083480 A1 also for imparting glyphosate tolerance; dicamba monooxygenase disclosed in U.S. Patent Application Publication No. 2003/0135879 A1 for imparting dicamba tolerance; a polynucleotide molecule encoding bromoxynil nitrilase (Bxn) disclosed in U.S. Pat. No. 4,810,648 for imparting bromoxynil tolerance; a polynucleotide molecule encoding phytoene desaturase (crtI) described in Misawa et al, (1993) *Plant J.* 4:833-840 and in Misawa et al, (1994) *Plant J.* 6:481-489 for norflurazon tolerance; a polynucleotide molecule encoding acetohydroxyacid synthase (AHAS, aka ALS) described in Sathasiivan et al. (1990) *Nucl. Acids Res.* 18:2188-2193 for imparting tolerance to sulfonylurea herbicides; polynucleotide molecules known as bar genes disclosed in DeBlock, et al. (1987) *EMBO J.* 6:2513-2519 for imparting glufosinate and bialaphos tolerance; polynucleotide molecules disclosed in U.S. Patent Application Publication No. 2003/010609 A1 for imparting N-amino methyl phosphonic acid tolerance; polynucleotide molecules disclosed in U.S. Pat. No. 6,107,549 for imparting pyridine herbicide resistance; molecules and methods for imparting tolerance to multiple herbicides such as glyphosate, atrazine, ALS inhibitors, isoxoflutole and glufosinate herbicides are disclosed in U.S. Pat. No. 6,376,754 and U.S. Patent Application Publication No. 2002/0112260. Molecules and methods for imparting insect/nematode/virus resistance are disclosed in U.S. Pat. Nos. 5,250,515; 5,880,275; 6,506,599; 5,986,175 and U.S. Patent Application Publication No. 2003/0150017 A1, each are herein incorporated by reference.

Another embodiment of the present invention provides methods for delivering transgenic crop plants comprising two or more genetic factors giving enhanced traits using haploid breeding approaches. One goal of transgenic trait integration is to deliver one or more transgenic traits to a inbred and the typical backcross process involved multiple generations with selection at each generation for the one or more transgenic traits coupled with selection for the elite inbred, referred to as the recurrent parent. As product concepts move to transgenic trait stacks, comprising two or more transgenic traits, the trait integration process becomes exponentially more complicated because an increasing number of progeny must be screened in order to recover progeny with both the transgenic traits and, as relevant, desired percent of the recurrent parent genome (i.e., 95% recurrent parent) and minimized percent of the donor parent genome (i.e., reduce linkage drag). The methods included herein provide an advantage over the art by reducing the time required to deliver a stacked transgenic trait hybrid to market as well as providing the potential for reducing the number of plots needed to generate an elite crop plant comprising two or more transgenic traits. These methods can be applied at any point in a breeding program, wherein the "recurrent" parent can be segregating. In other aspects, the recurrent parent comprises one or more genetic factors. Further, depending on the degree of segregating in the starting material, sister line generation can occur in parallel to trait integration. Examples of stacking two or more genetic factors using a haploid approach can be seen in U.S. Patent Application Publication No. 20090070891 and is herein incorporated by reference in its entirety.

Other aspects of the various embodiments of the invention includes, transgenic plants, transgenic plant seeds, transgenic crops, plant products and byproducts having any of the nucleic acid or protein fragments described above. The invention also provides for various methods that use such fragments.

Embodiments of the present invention also contemplate that the trait-improving recombinant DNA provided herein can be used in combination with other recombinant DNA to create plants with multiple desired traits or a further enhanced trait. The combinations generated can include multiple copies of any one or more of the recombinant DNA constructs. These stacked combinations can be created by any method, including but not limited to cross breeding of transgenic plants, or multiple genetic transformations.

DNA vectors containing gene(s) of interest or fragments of genes disclosed in the sequence listing can be delivered into plant cells via one of the several methods known to those skilled in the art, including but not limited to protoplast transformation, biolistic bombardment and *Agrobacterium*-mediated transformation. The delivered DNA can be integrated randomly into a plant genome or can also be present as part of the independently segregating genetic units such as artificial chromosome or mini-chromosome. One aspect of this embodiment, the construct further comprises regulatory sequences, including, for example, a promoter, operably linked to the sequence.

Plant Cell Transformation Methods

Numerous methods for transforming chromosomes in a plant cell nucleus with recombinant DNA are known in the art and are used in methods of preparing a transgenic plant cell nucleus cell, and plant. Two effective methods for such transformation are *Agrobacterium*-mediated transformation and microprojectile bombardment. Microprojectile bombardment methods are illustrated in U.S. Pat. Nos. 5,015,580 (soybean); 5,550,318 (corn); 5,538,880 (corn); 5,914,451 (soybean); 6,160,208 (corn); 6,399,861 (corn); 6,153,812 (wheat) and 6,365,807 (rice) and *Agrobacterium*-mediated transformation is described in U.S. Pat. Nos. 5,159,135 (cotton); 5,824,877 (soybean); 5,463,174 (canola); 5,591,616 (corn); 5,846,797 (cotton); 6,384,301 (soybean), 7,026,528 (wheat) and 6,329,571 (rice), U.S. Patent Application Publication 2004/0087030 A1 (cotton), and U.S. Patent Application Publication 2001/0042257 A1 (sugar beet), all of which are incorporated herein by reference for enabling the production of transgenic plants. Transformation of plant material is practiced in tissue culture on a nutrient media, e.g., a mixture of nutrients that will allow cells to grow in vitro. Recipient cell targets include, but are not limited to, meristem cells, hypocotyls, calli, immature embryos and gametic cells such as microspores, pollen, sperm and egg cells. Callus can be initiated from tissue sources including, but not limited to, immature embryos, hypocotyls, seedling apical meristems, microspores and the like. Cells containing a transgenic nucleus are grown into transgenic plants.

In addition to direct transformation of a plant material with a recombinant DNA, a transgenic plant cell nucleus can be prepared by crossing a first plant having cells with a transgenic nucleus with recombinant DNA with a second plant lacking the transgenic nucleus. For example, recombinant DNA can be introduced into a nucleus from a first plant line that is amenable to transformation to transgenic nucleus in cells that are grown into a transgenic plant which can be crossed with a second plant line to introgress the recombinant DNA into the second plant line. A transgenic plant with recombinant DNA providing an enhanced trait, e.g. enhanced yield, can be crossed with transgenic plant line having other recombinant DNA that confers another trait, for example herbicide resistance or pest resistance, to produce progeny plants having recombinant DNA that confers both traits. Typically, in such breeding for combining traits the transgenic plant donating the additional trait is a male line and the transgenic plant carrying the base traits is the female line. The progeny of this cross will segregate such that some of the plants will carry the DNA for both parental traits and some will carry DNA for one parental trait; such plants can be identified by markers associated with parental recombinant DNA, e.g. marker identification by analysis for recombinant DNA or, in the case where a selectable marker is linked to the recombinant, by application of the selecting agent such as a herbicide for use with a herbicide tolerance marker, or by selection for the enhanced trait. Progeny plants carrying DNA for both parental traits can be crossed back into the female parent line multiple times, for example usually 6 to 8 generations, to produce a progeny plant with substantially the same genotype as one original transgenic parental line but for the recombinant DNA of the other transgenic parental line.

In certain embodiments of the invention the recombinant DNA insertion is "targeted" in order to achieve site-specific integration, for example to replace an existing gene in the genome, to use an existing promoter in the plant genome, or to insert a recombinant polynucleotide at a predetermined site known to be active for gene expression. Several site specific recombination systems exist which are known to function implants include cre-lox as disclosed in U.S. Pat. No. 4,959,317 and FLP-FRT as disclosed in U.S. Pat. No. 5,527,695, both incorporated herein by reference.

Transformation methods of this invention can be practiced in tissue culture on media and in a controlled environment. "Media" refers to the numerous nutrient mixtures that are used to grow cells in vitro, that is, outside of the intact living organism. Recipient cell targets include, but are not limited to, meristem cells, callus, immature embryos and gametic cells such as microspores, pollen, sperm and egg cells. It is contemplated that any cell from which a fertile plant can be regenerated is useful as a recipient cell. Callus can be initiated from tissue sources including, but not limited to, immature embryos, seedling apical meristems, microspores and the like. Cells capable of proliferating as callus are also recipient cells for genetic transformation. Practical transformation methods and materials for making transgenic plants of this invention, for example, various media and recipient target cells, transformation of immature embryo cells and subsequent regeneration of fertile transgenic plants are disclosed in U.S. Pat. Nos. 6,194,636 and 6,232,526, which are incorporated herein by reference.

The seeds of transgenic plants can be harvested from fertile transgenic plants and be used to grow progeny generations of transformed plants of this invention including hybrid plants line for selection of plants having an enhanced trait. In addition to direct transformation of a plant with a recombinant DNA, transgenic plants can be prepared by crossing a first plant having a recombinant DNA with a second plant lacking the DNA. For example, recombinant DNA can be introduced into first plant line that is amenable to transformation to produce a transgenic plant which can be crossed with a second plant line to introgress the recombinant DNA into the second plant line. A transgenic plant with recombinant DNA providing an enhanced trait, e.g. enhanced yield, can be crossed with transgenic plant line having other recombinant DNA that confers another trait, for example herbicide resistance or pest resistance, to produce progeny plants having recombinant DNA that confers both traits. Typically, in such breeding for combining traits the transgenic plant donating the additional trait is a male line and the transgenic plant carrying the base traits is the female line. The progeny of this cross will segregate such that some of the plants will carry the DNA for both parental traits and some will carry DNA for one parental trait; such plants can be identified by markers associated with parental recombinant DNA, e.g. marker identification by analysis for recombinant DNA or, in the case where a selectable marker is linked to the recombinant, by application of the selecting agent such as a herbicide for use with a herbicide tolerance marker, or by selection for the enhanced trait. Progeny plants carrying DNA for both parental traits can be crossed back into the female parent line multiple times, for example usually 6 to 8 generations, to produce a progeny plant with substantially the same genotype as one original transgenic parental line but for the recombinant DNA of the other transgenic parental line.

Descriptions of commonly used breeding terms such as "crossing", "hybrids" and methods for crossing and producing hybrid that are used to describe present invention can be found in one of several reference books (Allard, "Principles of Plant Breeding," John Wiley & Sons, NY, U. of CA, Davis, C A, 50-98, 1960; *Simmonds*, "Principles of crop improvement," Longman, Inc., NY, 369-399, 1979; Sneep and Hendriksen, "Plant breeding perspectives," Wageningen (ed), *Center for Agricultural Publishing and Documentation*, 1979; Fehr, In: Soybeans: Improvement, Production and Uses, 2nd Edition, Monograph., 16:249, 1987; Fehr, "Principles of variety development," *Theory and Technique*, (Vol. 1) and *Crop Species Soybean* (Vol. 2), Iowa State Univ., Macmillan Pub. Co., NY, 360-376, 1987).

In some embodiments of the invention, during transformation, DNA is introduced into only a small percentage of target plant cells in any one transformation. Marker genes are used to provide an efficient system for identification of those cells that are stably transformed by receiving and integrating a transgenic DNA construct into their genomes. Marker genes provide selective markers which confer resistance to a selective agent, such as an antibiotic or herbicide. Any of the herbicides to which plants of this invention can be resistant are useful agents for selective markers. Potentially transformed cells are exposed to the selective agent. In the population of surviving cells will be those cells where, generally, the resistance-conferring gene is integrated and expressed at sufficient levels to permit cell survival. Cells can be tested further to confirm stable integration of the exogenous DNA. Commonly used selective marker genes include those conferring resistance to antibiotics such as kanamycin and paromomycin (nptII), hygromycin B (aph IV) and gentamycin (aac3 and aacC4) or resistance to herbicides such as glufosinate (bar or pat) and glyphosate (aroA or EPSPS). Examples of such selectable are illustrated in U.S. Pat. Nos. 5,550,318; 5,633,435; 5,780,708 and 6,118,047, all of which are incorporated herein by reference. Selectable markers which provide an ability to visually identify transformants can also be employed, for example, a gene expressing a colored or fluorescent protein such as a luciferase or green fluorescent protein (GFP) or a gene expressing a beta glucuronidase or uidA gene (GUS) for which various chromogenic substrates are known.

Plant cells that survive exposure to the selective agent, or plant cells that have been scored positive in a screening assay, can be cultured in regeneration media and allowed to mature into plants. Developing plantlets regenerated from transformed plant cells can be transferred to plant growth mix, and hardened off, for example, in an environmentally controlled chamber at about 85% relative humidity, 600 ppm $CO_2$, and 25-250 microeinsteins $m^{-2}s^{-1}$ of light, prior to transfer to a greenhouse or growth chamber for maturation. Plants are regenerated from about 6 weeks to 10 months after a transformant is identified, depending on the initial tissue. Plants can be pollinated using conventional plant breeding methods known to those of skill in the art and seed produced. The regenerated transformed plant or its progeny seed or plants can be tested for expression of the recombinant DNA and selected for the presence of enhanced agronomic trait.

Progeny can be recovered from transformed plants and tested for expression of the exogenous recombinant polynucleotide. Useful assays include, for example, "molecular biological" assays, such as Southern and Northern blotting and PCR; "biochemical" assays, such as detecting the presence of RNA, e.g., double stranded RNA, or a protein product, e.g., by immunological means (ELISAs and Western blots) or by enzymatic function; plant part assays, such as leaf or root assays; and also, by analyzing the phenotype of the whole regenerated plant.

Transgenic Plants and Seeds

Transgenic plants derived from the plant cells of this invention are grown to generate transgenic plants having an enhanced trait as compared to a control plant and produce transgenic seed and haploid pollen of this invention. Such plants with enhanced traits are identified by selection of transformed plants or progeny seed for the enhanced trait. For efficiency a selection method is designed to evaluate multiple transgenic plants (events) including the recombinant DNA, for example multiple plants from 2 to 20 or more transgenic events. Transgenic plants grown from transgenic seed provided herein demonstrate improved agronomic traits that contribute to increased yield or other trait that provides increased plant value, including, for example, improved seed quality. Of particular interest are plants having enhanced water use efficiency, enhanced cold tolerance, increased yield, enhanced nitrogen use efficiency, enhanced seed protein and enhanced seed oil. Transgenic plants of the present invention include, but are not limited to, corn, soybean, cotton, canola, alfalfa, wheat, rice, sugarcane, sugar beet seed, millet, barley, peanut, pigeon pea, sorghum, vegetables (including but not limited to Broccoli, Cauliflower, Cabbage, Radish, Chinese cabbage, Melons, Watermelons, Cucumber, Gourds, Pumpkin, Squash, Pepper, Tomato, Eggplant, Onion, Carrot, Garden Bean, Sweet Corn, Pea, Dry Bean, Okra, Spinach, Leek, Lettuce, and Fennel), grape, berries (including blue, black, raspberry, mullberry, boysenberry. . . etc), cherry and related fruit trees (including but not limited to plum, peach, apricot, kiwi, pomegranate, mango, fig), fruit trees (including but not limited to orange, lemon, lime, blood orange, grapefruit, and the like), nut trees (including but not limited to coconut, walnut (English and black), pecan, almond, hazelnut, brazil nut, hickory nut, acorn, and the like), sunflower, other oilseed producing plants or any combinations thereof.

Selection Methods for Transgenic Plants with Enhanced Agronomic Trait

Within a population of transgenic plants each regenerated from a plant cell having a nucleus with recombinant DNA many plants that survive to fertile transgenic plants that produce seeds and progeny plants may not exhibit an enhanced agronomic trait. Selection from such population is necessary to identify one or more transgenic plant cells having a transgenic nucleus that can provide plants with the enhanced trait. Transgenic plants having enhanced traits are selected from populations of plants regenerated or derived from plant cells transformed as described herein by evaluating the plants in a variety of assays to detect an enhanced trait. These assays also can take many forms including, but not limited to, direct screening for the trait in a greenhouse or field trial or by screening for a surrogate trait. Such analyses can be directed to detecting changes in the chemical composition, biomass, physiological properties, morphology of the plant. Changes in chemical compositions such as nutritional composition of grain can be detected by analysis of the seed composition and content of protein, free amino acids, oil, free fatty acids, starch or tocopherols. Changes in biomass characteristics can be made on greenhouse or field grown plants and can include plant height, stem diameter, root and shoot dry weights; and, for corn plants, ear length and diameter. Changes in physiological properties can be identified by evaluating responses to stress conditions, for example assays using imposed stress conditions such as water deficit, nitrogen deficiency, cold growing conditions, pathogen or insect attack or light deficiency, or increased plant density. Changes in morphology can be measured by visual observation of tendency of a transformed plant with an enhanced agronomic trait to also appear to be a normal plant as compared to changes toward bushy, taller, thicker, narrower leaves, striped leaves, knotted trait, chlorosis, albino, anthocyanin production, or altered tassels, ears or roots. Other selection properties include days to pollen shed, days to silking, leaf extension rate, chlorophyll content, leaf temperature, stand, seedling vigor, internode length, plant height, leaf number, leaf area, tittering, brace roots, stay green, stalk lodging, root lodging, plant health, barreness/prolificacy, green snap, and pest resistance. In addition, phenotypic characteristics of harvested grain can be evaluated, including number of kernels per row on the ear, number of rows of kernels on the ear, kernel abortion, kernel weight, kernel size, kernel density and physical grain quality.

Assays for screening for a desired trait are readily designed by those practicing in the art. The following illustrates screening assays for corn traits using hybrid corn plants. The assays can be readily adapted for screening other plants such as canola, cotton and soybean either as hybrids or inbreds.

In certain embodiments of the invention transgenic corn plants having nitrogen use efficiency can be identified by screening in fields with three levels of nitrogen (N) fertilizer being applied, e.g. low level (0 N), medium level (80 lb/ac) and high level (180 lb/ac). Plants with enhanced nitrogen use efficiency provide higher yield as compared to control plants.

In some embodiments, the present invention discloses transgenic plant exhibiting increased yield under various stress conditions (e.g., drought, heat, limited nitrogen, or any combinations thereof disclosed herein, compare to control plant. For example, transgenic plants of the present invention can exhibit averaged, or similar yield received in the past, but higher yield as compared the control plants under similar stress conditions. The present invention is capable of maintaining yield under stress conditions as compared with plants that do not comprise the genes or miRNA disclosed herein.

In other embodiments, transgenic corn plants having enhanced yield can be identified by screening using progeny of the transgenic plants over multiple locations with plants grown under optimal production management practices and maximum weed and pest control. A useful target for improved yield is a 5% to 10% increase in yield as compared to yield produced by plants grown from seed for a control plant. Selection methods can be applied in multiple and diverse geographic locations, for example up to 16 or more locations, over one or more planting seasons, for example at least two planting seasons, to statistically distinguish yield improvement from natural environmental effects.

In other embodiments, transgenic corn plants having enhanced water use efficiency can be identified by screening plants in an assay where water is withheld for a period to induce stress followed by watering to revive the plants. For example, a useful selection process imposes 3 drought/rewater cycles on plants over a total period of 15 days after an initial stress free growth period of 11 days. Each cycle consists of 5 days, with no water being applied for the first four days and a water quenching on the 5th day of the cycle. The primary phenotypes analyzed by the selection method are the changes in plant growth rate as determined by height and biomass during a vegetative drought treatment.

In other embodiments, transgenic corn plants having enhanced cold tolerance can be identified by screening plants in a cold germination assay and/or a cold tolerance field trial. In a cold germination assay trays of transgenic and control seeds are placed in a growth chamber at 9.7° C. for 24 days (no light). For example, seeds having higher germination rates as compared to the control can be identified as having enhanced cold tolerance. In a cold tolerance field trial plants with enhanced cold tolerance can be identified from field planting at an earlier date than conventional Spring planting for the field location. For example, seeds are planted into the ground around two weeks before local farmers begin to plant corn so that a significant cold stress is exerted onto the crop, named as cold treatment. Seeds can be planted under local optimal planting conditions such that the crop has little or no exposure to cold condition, named as normal treatment. At each location, seeds may be can be planted under both cold and normal conditions preferably with multiple repetitions per treatment.

In other embodiments, transgenic corn plants having seeds with increased protein and/or oil levels can be identified by analyzing progeny seed for protein and/or oil. Near-infrared transmittance spectrometry is a non-destructive, high-throughput method that is useful to determine the composition of a bulk seed sample for properties listed in table 1.

TABLE 1

| Typical sample(s): | Whole grain corn and soybean seeds |
|---|---|
| Typical analytical range: | Corn - moisture 5-15%, oil 5-20%, protein 5-30%, starch 50-75%, and density 1.0-1.3%. Soybean - moisture 5-15%, oil 15-25%, and protein 35-50%. |

Although the plant cells and methods of this invention can be applied to any plant cell, plant, seed or pollen, e.g. any fruit, vegetable, grass, tree or ornamental plant, the various aspects of the invention are preferably applied to corn, soybean, cotton, canola, alfalfa, wheat, rice, sugarcane, and sugar beet plants. In many cases the invention is applied to corn plants that are inherently resistant to disease from the Mal de Rio Cuarto virus or the *Puccina sorghi* fungus or both.

Homolog Identification

In certain embodiment, the present invention also includes identification of homologs of proteins encoded by the DNA identified in the sequence listing which is used to provide transgenic seed and plants having enhanced agronomic traits. From the sequence of the homologs, homologous DNA sequence are identified for preparing additional transgenic seeds and plants of this invention with enhanced agronomic traits.

An "All Protein Database" are constructed of known protein sequences using a proprietary sequence database and the National Center for Biotechnology Information (NCBI) non-redundant amino acid database (nr.aa). For each organism from which a polynucleotide sequence provided herein can be obtained, an "Organism Protein Database" are constructed of known protein sequences of the organism; it is a subset of the All Protein Database based on the NCBI taxonomy ID for the organism.

The All Protein Database are queried using amino acid sequences provided herein as SEQ ID NO: 91968 through SEQ ID NO: 183370 using NCBI "blastp" program with E-value cutoff of $1e^{-8}$. Up to 1000 top hits are kept, and separated by organism names. For each organism other than that of the query sequence, a list is kept for hits from the query organism itself with a more significant E-value than the best hit of the organism. The list contain likely duplicated genes of the polynucleotides provided herein, and is referred to as the Core List. Another list is kept for all the hits from each organism, sorted by E-value, and referred to as the Hit List.

The Organism Protein Database are queried using polypeptide sequences provided herein as SEQ ID NO: 91968 through SEQ ID NO: 183370 using NCBI "blastp" program with E-value cutoff of $1e^{-4}$. Up to 1000 top hits are kept. A BLAST searchable database is constructed based on these hits, and are referred to as "SubDB". SubDB are queried with each sequence in the Hit List using NCBI "blastp" program with E-value cutoff of $1e^{-8}$. The hit with the best E-value are compared with the Core List from the corresponding organism. The hit is deemed a likely ortholog if it belongs to the Core List, otherwise it is deemed not a likely ortholog and there is no further search of sequences in the Hit List for the same organism. Homologs from a large number of distinct organisms are identified and reported.

Recombinant DNA constructs can be prepared using the DNA encoding each of the identified homologs and the constructs can be used to prepare multiple events of transgenic corn, soybean, canola, cotton and other transgenic plants mentioned. Plants can be regenerated from the transformed plant cells and used to produce progeny plants and seed that are screened for enhanced water use efficiency, enhanced cold tolerance, increased yield, enhanced nitrogen use efficiency, enhanced seed protein and enhanced seed oil. From each group of multiple events of transgenic plants with a specific recombinant DNA for a homolog the event that produces the greatest enhancement in yield, water use efficiency, nitrogen use efficiency, enhanced cold tolerance, enhanced seed protein and enhanced seed oil is identified and progeny seed can be selected for commercial development.

Pfam Module Annotation

The amino acid sequence of the expressed proteins shown to be associated with an enhanced trait are analyzed for Pfam protein family against the current Pfam collection of multiple sequence alignments and hidden Markov models using the HMMER software in the appended computer listing. The Pfam domain modules and individual protein domain for the proteins shown in the sequence listing. The Hidden Markov model databases for the identified patent families are known to a skilled artisan allowing identification of other homologous proteins and their cognate encoding DNA to enable the full breadth of the invention for a person of ordinary skill in the art. Certain proteins are identified by a single Pfam domain and others by multiple Pfam domains.

Selectable Markers

The present invention includes transgenic plants with and without selectable markers. As used herein the term "marker" refers to any transcribable polynucleotide molecule whose expression, or lack thereof, can be screened for or scored in some way. Marker genes for use in the practice of the present invention include, but are not limited to transcribable polynucleotide molecules encoding B-glucuronidase (GUS described in U.S. Pat. No. 5,599,670, which is incorporated herein by reference), green fluorescent protein and variants thereof (GFP described in U.S. Pat. Nos. 5,491,084 and 6,146,826, RFP and the like), proteins that confer antibiotic resistance, or proteins that confer herbicide tolerance. Marker genes in genetically modified plants are generally of two types: genes conferring antibiotic resistance or genes conferring herbicide tolerance. Examples include, but are not limited to antibiotic resistance markers, including those encoding proteins conferring resistance to kanamycin (nptII), hygromycin B (aph IV), streptomycin or spectinomycin (aad, spec/strep) and gentamycin (aac3 and aacC4) are known in the art.

Included within the term "selectable markers" are also genes which encode a secretable marker whose secretion can be detected as a means of identifying or selecting for transformed cells. Examples include markers that encode a secretable antigen that can be identified by antibody interaction, or even secretable enzymes which can be detected catalytically. Selectable secreted marker proteins fall into a number of classes, including small, diffusible proteins which are detectable, (e.g., by ELISA), small active enzymes which are detectable in extracellular solution (e.g., alpha.-amylase, beta.-lactamase, phosphinothricin transferase), or proteins which are inserted or trapped in the cell wall (such as proteins which include a leader sequence such as that found in the expression unit of extension or tobacco PR-S). Other possible selectable marker genes will be apparent to those of skill in the art.

The selectable marker is preferably GUS, green fluorescent protein (GFP) or variants thereof, neomycin phosphotransferase II (nptII), luciferase (LUX), an antibiotic resistance protein, or a herbicide (e.g., glyphosate, bromoxynil, and the like) resistance or tolerance protein. The selectable marker is most preferably a kanamycin, hygromycin, or herbicide resistance marker.

In one aspect, the present invention includes recombinant DNA constructs having a polynucleotide encoding a protein that has an amino acid sequence having at least 95% identity over at least 95% of the length of a reference sequence selected from the group consisting of SEQ ID NO: 91968-183370 when said amino acid sequence is aligned with said reference sequence.

In another aspect, the present invention includes a mixture having plant cells, and an antibody to a protein produced in said cells wherein said protein has an amino acid sequence that has at least 95% identity over at least 95% of the length of a reference sequence selected from the group consisting of SEQ ID NO: 91968-183370 when said amino acid sequence is aligned to said reference sequence.

Yet another aspect of the present invention includes recombinant DNA constructs having a promoter that is functional in a plant cell and that is operably linked to a polynucleotide that: (a) encodes a protein having an amino acid sequence having at least 95% identity over at least 95% of the length of a reference sequence selected from the group consisting of SEQ ID NO: 91968-183370, when said amino acid sequence is aligned to said reference sequence; or is transcribed into an RNA molecule that suppresses the level of an endogenous protein that has an amino acid sequence that is at least 95% identical over at least 95% of the length of a reference sequence of SEQ ID NO: 91968-183370, when said amino acid sequence is aligned to said reference sequence; and wherein said construct is stably integrated into a chromosome in a plant cell nucleus. In some aspect, this invention includes a transgenic plant cell having the recombinant DNA construct wherein said DNA construct provides for an enhanced trait as compared to control plants; and wherein said enhanced trait is enhanced water use efficiency, enhanced cold tolerance, increased yield, enhanced nitrogen use efficiency, enhanced seed protein or enhanced seed oil. The DNA construct further can express a protein that provides tolerance from exposure to an herbicide (e.g., a glyphosate, dicamba, or glufosinate compound) having an agent applied at levels that are lethal to a wild type of said plant cell nucleus.

In some aspects, this invention provides transgenic plants (e.g., corn, soybean, cotton, canola, alfalfa, wheat, rice, sugarcane, or sugar beet plant), that is homozygous for said recombinant DNA and have a plurality of plant cells.

Yet in another aspect, this inventions includes transgenic pollen grains having a haploid derivative of a plant cell nucleus having a chromosome comprising the recombinant DNA construct.

In one aspect, this inventions provides a method for manufacturing non-natural, transgenic seed (e.g., corn, soybean, cotton, canola, alfalfa, wheat, rice, sugarcane, or sugar beet seed) that can be used to produce a crop of transgenic plants with an enhanced trait resulting from expression of a stably-integrated, recombinant DNA construct, said method includes (a) screening a population of plants for said enhanced trait and said recombinant DNA, wherein individual plants in said population exhibit said trait at a level less than, essentially the same as or greater than the level that said trait is exhibited in control plants which do not contain said recombinant DNA, wherein said enhanced trait is selected from the group of enhanced traits consisting of enhanced water use efficiency, enhanced cold tolerance, increased yield, enhanced nitrogen use efficiency, enhanced seed protein and enhanced seed oil; (b) selecting from said population one or more plants that exhibit said trait at a level greater than the level that said trait is exhibited in control plants, and (c) collecting seed from selected plant from step b.

Yet in another aspect, the method of this invention further includes: (a) verifying that said recombinant DNA is stably integrated in said selected plants, and (b) analyzing tissue of said selected plant to determine the expression or suppression of a protein having the function of a protein having an amino acid sequence selected from the group consisting of one of SEQ ID NOs: 91968-183370.

In one aspect, this invention provides a method of producing hybrid corn seed including: (a) acquiring hybrid corn seed from an herbicide tolerant corn plant which also has a stably-integrated, recombinant DNA construct; (b) producing corn plants from said hybrid corn seed, wherein a fraction of the plants produced from said hybrid corn seed is homozygous for said recombinant DNA, a fraction of the plants produced from said hybrid corn seed is hemizygous for said recombinant DNA, and a fraction of the plants produced from said hybrid corn seed has none of said recombinant DNA; (c) selecting corn plants which are homozygous and hemizygous for said recombinant DNA by treating with an herbicide; (d) collecting seed from herbicide-treated-surviving corn plants and planting said seed to produce further progeny corn plants; (e) repeating steps (c) and (d) at least once to produce an inbred corn line; and (f) crossing said inbred corn line with a second corn line to produce hybrid seed.

In some aspect, this invention provides substantially purified nucleic acid molecule having a nucleic acid sequence wherein said nucleic acid sequence exhibits 95% or greater identity to a nucleic acid sequence selected from the group consisting of SEQ ID NO: 1 through SEQ ID NO: 91967 and sequences complementary to SEQ ID NO: 1 through SEQ ID NO: 91967.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US09012723B2). An electronic copy of the "Sequence Listing" will also be available from the USPTO upon request and payment of the fee set forth in 37 CFR 1.19(b)(3).

What is claimed is:

1. A recombinant DNA construct comprising an exogenous promoter operably linked to a polynucleotide that encodes a non-coding RNA molecule, wherein said non-coding RNA molecule is capable of binding to an RNA encoding a polypeptide having at least 90% identity to SEQ ID NO: 129,017, and wherein said non-coding RNA molecule suppresses the expression of said polypeptide.

2. A transgenic plant cell comprising the recombinant DNA construct of claim 1.

3. The transgenic plant cell of claim 2 further comprising DNA expressing a protein that provides tolerance from exposure to an herbicide.

4. The transgenic plant cell of claim 3 wherein said herbicide comprises a glyphosate, dicamba, or glufosinate compound.

5. A transgenic plant comprising a plurality of the transgenic plant cells of claim 2.

6. The transgenic plant of claim 5 which is homozygous for said recombinant DNA.

7. A transgenic seed comprising a plurality of the transgenic plant cells of claim 2.

8. The transgenic seed of claim 7, wherein said seed is a corn, soybean, cotton, canola, alfalfa, wheat, rice, sugarcane, or sugar beet seed.

9. A method for manufacturing non-natural, transgenic seed comprising the recombinant DNA construct of claim 1, said method comprising:
 (a) screening a population of plants for said recombinant DNA construct;
 (b) selecting from said population one or more plants that comprise said recombinant DNA construct, and
 (c) collecting seed from selected one or more plants from step b.

10. The method of claim 9 wherein said method for manufacturing said transgenic seed further comprises analyzing a tissue of said selected one or more plants to determine the suppression of said polypeptide.

11. The method of claim 10, wherein said seed is a corn, soybean, cotton, canola, alfalfa, wheat, rice, sugarcane, or sugar beet seed.

12. The transgenic plant cell of claim 2, wherein said polypeptide has at least 92% sequence identity to SEQ ID NO: 129,017.

13. The transgenic plant cell of claim 12, wherein said polypeptide has at least 95% sequence identity to SEQ ID NO: 129,017.

14. The transgenic plant cell of claim 13, wherein said polypeptide has at least 98% sequence identity to SEQ ID NO: 129,017.

15. The transgenic plant cell of claim 2, wherein said polypeptide comprises at least 15 contiguous amino acid residues identical to said SEQ ID NO: 129,017.

16. The transgenic plant cell of claim 15, wherein said polypeptide comprises at least 20 contiguous amino acid residues identical to said SEQ ID NO: 129,017.

17. A recombinant DNA construct comprising an exogenous promoter operably linked to a polynucleotide encoding a microRNA or ta-siRNA that is capable of binding to and suppressing the expression of a RNA molecule comprising a sequence having at least 90% sequence identity to SEQ ID NO: 37,332.

18. The recombinant DNA construct of claim 17, wherein said polynucleotide comprises at least 20, 21, 22, 23, 24, 25, 26, 27, 28, 29, 30 or more consecutive nucleotides of SEQ ID NO: 37,332.

19. A transgenic cell, plant, or seed comprising said recombinant DNA construct of claim 17.

20. The transgenic cell of claim 2, wherein said non-coding RNA molecule is a double-stranded RNA, an antisense RNA, a microRNA, or a ta-siRNA.

21. A soybean cell, plant, or seed comprising a transgene or mutation, wherein said transgene or mutation reduces the level or activity of a polypeptide having at least 90% identity to SEQ ID NO: 129,017, wherein said transgene encodes a microRNA or ta-siRNA.

22. The soybean cell, plant, or seed of claim 21, wherein said soybean cell, plant, or seed comprises an insertion mutation in an endogenous gene encoding said polypeptide.

23. The soybean cell, plant, or seed of claim 22, wherein said insertion mutation is created by a transposable element or T-DNA.

* * * * *

UNITED STATES PATENT AND TRADEMARK OFFICE
CERTIFICATE OF CORRECTION

PATENT NO. : 9,012,723 B2
APPLICATION NO. : 13/138181
DATED : April 21, 2015
INVENTOR(S) : Liang Guo et al.

Page 1 of 1

It is certified that error appears in the above-identified patent and that said Letters Patent is hereby corrected as shown below:

On the title page, item 54 and in the specification, column 1, lines 1-5, please change "ISOLATED NOVEL ACID AND PROTEIN MOLECULES FROM SOY AND METHODS OF USING THOSE MOLECULES TO GENERATE TRANSGENE PLANTS WITH ENHANCED AGRONOMIC TRAITS" to --ISOLATED NOVEL NUCLEIC ACID AND PROTEIN MOLECULES FROM SOYBEANS AND METHODS OF USING THOSE MOLECULES TO GENERATE TRANSGENIC PLANTS WITH ENHANCED AGRONOMIC TRAITS--.

Signed and Sealed this
Twenty-seventh Day of October, 2015

Michelle K. Lee
*Director of the United States Patent and Trademark Office*